United States Patent
Jackson et al.

(10) Patent No.: US 11,273,231 B2
(45) Date of Patent: Mar. 15, 2022

(54) PACKAGING FOR USE IN A DECONTAMINATION SYSTEM

(71) Applicant: Medivators Inc., Plymouth, MN (US)

(72) Inventors: Mark Jackson, Great Wakering (GB); Gary Spencer, Rayleigh (GB)

(73) Assignee: Medivators Inc., Minneapolis, MN (US)

( * ) Notice: Subject to any disclaimer, the term of this patent is extended or adjusted under 35 U.S.C. 154(b) by 250 days.

(21) Appl. No.: 16/629,365

(22) PCT Filed: Jun. 26, 2018

(86) PCT No.: PCT/US2018/039394
§ 371 (c)(1),
(2) Date: Jan. 8, 2020

(87) PCT Pub. No.: WO2019/013966
PCT Pub. Date: Jan. 17, 2019

(65) Prior Publication Data
US 2021/0128768 A1    May 6, 2021

Related U.S. Application Data

(60) Provisional application No. 62/530,439, filed on Jul. 10, 2017.

(51) Int. Cl.
*A61L 2/26* (2006.01)
*A61B 50/33* (2016.01)
(Continued)

(52) U.S. Cl.
CPC ................ *A61L 2/26* (2013.01); *A61B 50/33* (2016.02); *A61L 2/20* (2013.01); *A61L 2/208* (2013.01); *A61B 2050/007* (2016.02); *A61L 2101/02* (2020.08); *A61L 2101/36* (2020.08); *A61L 2202/121* (2013.01); *A61L 2202/122* (2013.01);
(Continued)

(58) Field of Classification Search
None
See application file for complete search history.

(56) References Cited

U.S. PATENT DOCUMENTS 5,882,589 A    3/1999   Mariotti
5,993,754 A *  11/1999  Lemmen ............... A61L 2/26
                                              422/293

(Continued)

FOREIGN PATENT DOCUMENTS

WO    20150179824    11/2015
WO    20160176442    11/2016

OTHER PUBLICATIONS

International Preliminary Report on Patentability of the International Searching Authority Dated Jan. 23, 2020, of International PCT Application No. PCT/US2018/039394 filed Jun. 26, 2018.
(Continued)

*Primary Examiner* — Holly Kipouros

(57) ABSTRACT

An apparatus for use in a method of decontaminating a device including a tray. A membrane permeable by a decontaminating fluid is positioned over the top of the tray to form an enclosed space. A lid is secured to the tray and the membrane is positioned between the tray and the lid. A hub assembly is positioned within the tray.

20 Claims, 7 Drawing Sheets

(51) Int. Cl.
    *A61L 2/20*           (2006.01)
    *A61L 101/36*        (2006.01)
    *A61B 50/00*         (2016.01)
    *A61L 101/02*        (2006.01)

(52) U.S. Cl.
    CPC ..... *A61L 2202/123* (2013.01); *A61L 2202/24* (2013.01)

(56) References Cited

U.S. PATENT DOCUMENTS

| | | |
|---|---|---|
| 7,467,890 B2 | 12/2008 | Patzek, IV |
| 2008/0187465 A1* | 8/2008 | Horacek ................ A61B 50/20 422/300 |
| 2010/0049156 A1* | 2/2010 | Dickhorner ............... F26B 5/06 604/403 |
| 2011/0139650 A1* | 6/2011 | Dworak ................. B65B 55/18 206/363 |

OTHER PUBLICATIONS

International Search Report and Written Opinion of the International Searching Authority dated Oct. 17, 2018, of International PCT Application No. PCT/US2018/039394 filed Jun. 26, 2018.

* cited by examiner

PACKAGING FOR USE IN A DECONTAMINATION SYSTEM

CROSS REFERENCE TO RELATED APPLICATIONS

This application claims priority to U.S. Provisional Patent Application No. 62/530,439 filed Jul. 10, 2017.

TECHNICAL FIELD

The instant disclosure relates to packaging for use in a decontamination system and methods of using the same. In some embodiments, the packaging may be terminal packaging for a device, such as a lumen medical device.

BACKGROUND

Devices that include elongated and/or tortious flow paths often present certain challenges for decontamination. An example of a device that has an elongated flow path that may require repeated decontamination processing is an endoscope, an optical instrument that is used to inspect and treat interior portions of the body. Endoscopes have elongated lumens, flexible transparent fibers that transmit light and a method of imaging to provide a view to the observer. Endoscopes may present certain problems in that such devices typically have numerous exterior crevices and interior lumens which can harbor microbes. Microbes can be found on surfaces in such crevices and interior lumens as well as on exterior surfaces of the endoscope. Other medical or dental instruments which comprise lumens, crevices, and the like can also provide challenges for decontaminating various internal and external surfaces that can harbor microbes.

Additionally, after a device is subjected to a decontamination cycle, it may be desirable to keep the device in an environment that maintains the decontaminated state. For example, after decontamination of a medical device, it may be desirable to store or maintain the device in the decontaminated state until the device is to be used.

Thus, there is a need for a decontamination apparatus or process that can decontaminate a device, such as a lumen device, without risking damage to the device. Further, it may be desirable that the apparatus or process also enables storage of the device following the decontamination.

SUMMARY

An apparatus for use in a method of decontaminating a device includes a tray. A membrane permeable by a decontaminating fluid is positioned over the top of the tray to form an enclosed space. A lid is secured to the tray and the membrane is positioned between the tray and the lid. A hub assembly is positioned within the tray.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Devices, such as medical devices, can be decontaminated or sterilized at relatively low temperatures using hydrogen peroxide ($H_2O_2$) and/or peracetic acid (PAA) chemistry. In such systems, the chemistry may be provided as a vapor into a decontamination chamber containing the device to be decontaminated. Devices containing a lumen may be particularly challenging to decontaminate as the decontaminating substance must flow through the lumen to decontaminate the surface. The term "decontamination" is used herein in preference to the term "sterility" since the latter implies the complete absence of pathogenic organisms. One skilled in the art will appreciate that the ultimate aim of a decontamination system for medical equipment may be to get as close as possible to sterility and sterility is a decontamination process. Additionally, although the present packaging system and decontamination method will be described with respect to an endoscope, a flexible lumen-containing medical device, it will be appreciated that the described system and method may be applied to substantially any type of device including medical, surgical, dental and veterinary equipment, apparatus and instruments, which may or may not include a lumen.

Figure 1:
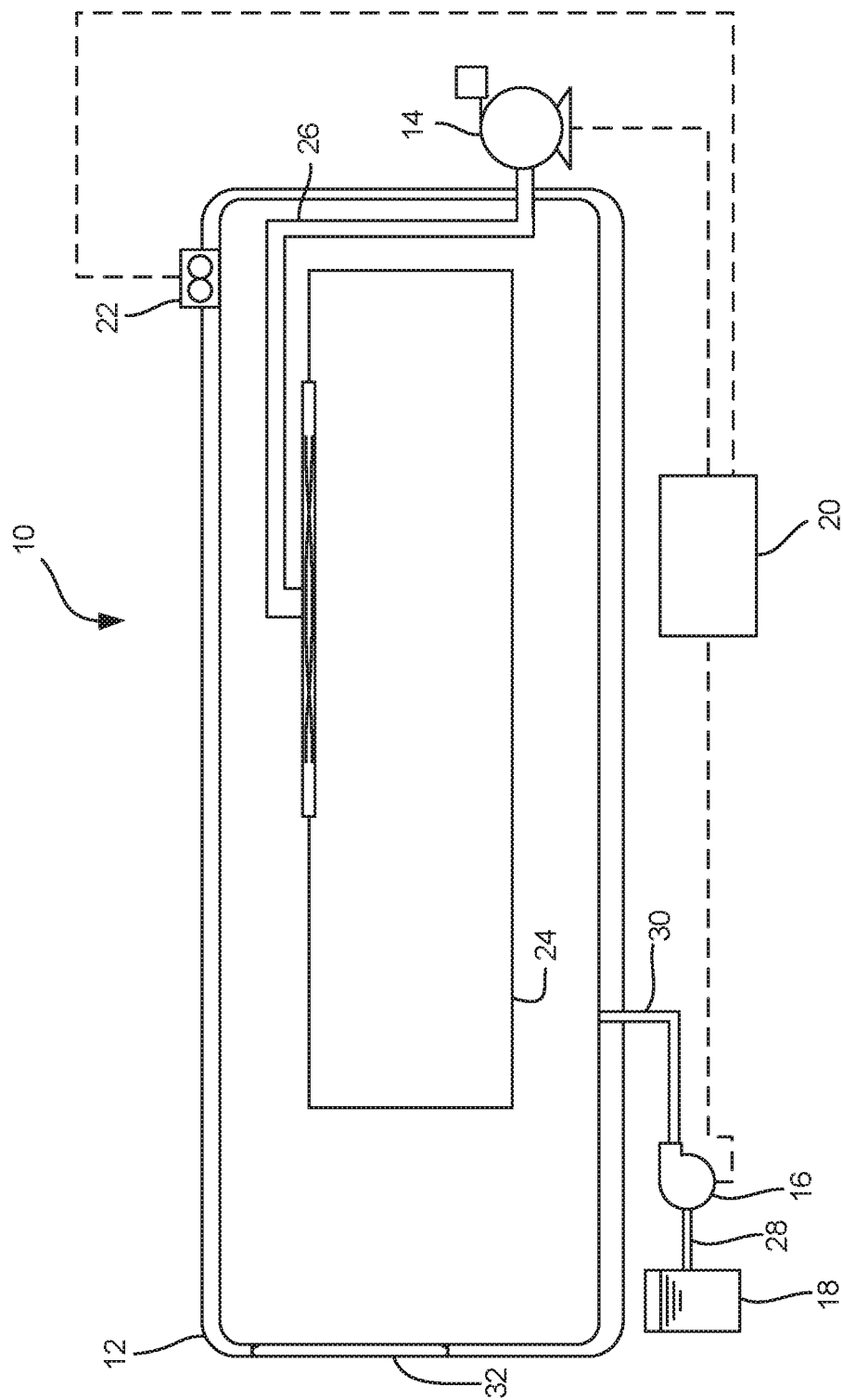
FIG. 1 is a schematic diagram of an exemplary decontamination system.

FIG. 1 is a schematic view of a decontamination system 10 which includes a decontamination chamber 12, a vacuum pump 14, a vaporizer 16, a source of decontaminating substance 18, a controller 20, and a vent 22. Packaging assembly 24 containing a device, such as a lumen device, is positioned within decontamination chamber 12.

The vaporizer 16 and the source of decontaminating substance 18 are located outside of the decontamination chamber 12 and are connected to one another by conduit 28. Conduit 30 connects the vaporizer 16 to the interior space of decontamination chamber 12. The controller 20 is connected to the vacuum pump 14, vaporizer 16, and vent 22 and is configured to control these items, for example during a decontamination cycle or process.

The decontamination chamber 12 defines an enclosed space. The decontamination chamber 12 includes a door 32 that is configured to accommodate inserting or removing items, such as the packaging assembly 24, into or out of the decontamination chamber 12. In some embodiments, the decontamination chamber 12 may include two doors which may be located on different or opposite sides of the decontamination chamber 12. Such a configuration may allow the packaging assembly 24 to "pass through" the decontamination chamber 12.

The decontamination chamber 12 can withstand pressure changes within the enclosed space as may be encountered during a decontamination cycle or process. The door 32 may be sealed and/or reinforced to provide a sealed environment within the decontamination chamber 12. For example, during a decontamination cycle the pressure within the enclosed space may be maintained at a pressure that is higher or lower than a pressure outside the decontamination chamber 12.

The vacuum pump 14 is positioned outside of the decontamination chamber 12 and is connected to the packaging assembly 24 by conduit 26. The vacuum pump 14 can be used to change the pressure within the decontamination chamber 12. For example, the vacuum pump 14 may draw gas or air from the decontamination chamber 12 to lower the pressure inside the decontamination chamber 12. The vacuum pump 14 may also be operated in the opposite manner such that the vacuum pump 14 forces gas into the decontamination chamber 12 to increase the pressure inside the decontamination chamber 12.

The decontamination chamber 12 also includes the vent 22, which may be placed in an open position (including a partially open position) or a closed position. When the vent 22 is in an open position, air can flow through the vent 22 and into or out of the decontamination chamber 12. For example, when the vent 22 is in the open position, air will flow through the vent 22 and the pressure inside the decontamination chamber 12 will equalize with the pressure outside the decontamination chamber 12. In some embodiments, the position of vent 22 may be coordinated with operation of the vacuum pump 14. For example, closing the vent 22 when the vacuum pump 14 is operated may cause the pressure within the decontamination chamber 12 to increase or decrease. Further, opening the vent 22 when the vacuum pump 14 is drawing air from within the decontamination chamber 12 results in air from outside the decontamination chamber 12 flowing through the decontamination chamber 12, which is referred to as an air flush. In some embodiments, the decontamination chamber 12 may not include a vent 22.

The decontaminating substance 18 is chemistry suitable for use in a decontamination or sterilization process. For example, the decontaminating substance 18 may include peracetic acid (PAA) and/or hydrogen peroxide ($H_2O_2$). In some embodiments, the decontaminating substance 18 may comply with the International Organization for Standardization (ISO) standard ISO/TC 198, Sterilization of Healthcare Products and/or the Association for the Advancement of Medical Instrumentation (AAMI) standard ANSI/AAMI/ISO 11140-1:2005, "Sterilization of Healthcare Products—Chemical Indicators—Part I: General Requirements" (Arlington, Va.: AAMI 2005). As described herein, decontaminating substance or fluid 18 may be dispersed within the decontamination chamber 12 as a liquid, a vapor, gas, or a combination thereof (such as a fog) during a decontamination process.

The vaporizer 16 can convert the decontaminating substance or fluid 18 into a vapor, fog, gas, or other suitable form for a decontamination process. For example, the vaporizer 16 may heat the decontaminating substance 18 provided in a liquid form to evaporate or otherwise transform the liquid decontaminating substance 18 into a vapor or gas. In an alternative configuration, the vaporizer 16 may convert the decontaminating substance 18 into a vapor or fog via a mechanical means such as an atomizing nozzle or a sprayer (e.g. the vaporizer may include an atomizer that uses a mechanical force such as rotating blades or air pressure to break up a stream of liquid decontaminating substance 18 into individual droplets and/or to produce an aerosol). The droplets or aerosol of decontaminating substance 18 may be released into the decontamination chamber 12 to form a vapor. The vaporizer 16 may be controlled to introduce the decontaminating substance 18 into the decontamination chamber 12 at a suitable temperature, pressure, relative humidity, and/or concentration.

In some embodiments, the decontaminating substance 18 may be kept at room temperature (e.g., 20° C. to 25° C.) before being provided to the vaporizer 16. Alternatively, the decontaminating substance 18 may be cooled or heated above or below room temperature before being provided to the vaporizer 16.

The controller 20 provides control signals to and/or receives condition sensing and equipment status signals from other elements of the decontamination system 10. For example, the controller 20 may include monitoring and control of the vaporizer 16, the vacuum pump 14, and the vent 22. The controller 20 may regulate delivery of the decontaminating substance 18 to the vaporizer 16. The controller 20 may be configured to adjust the environmental conditions within the decontamination chamber 12 by controlling the vacuum pump 14, the vent 22, and/or the vaporizer 16. For example, the controller 20 may control the vacuum pump 14 for adjustment of the pressure of the decontamination chamber 12. The controller 20 may control the vaporizer 16 for adjustment of the relative humidity, the temperature, and/or the concentration of decontaminating substance 18 within the decontamination chamber 12.

Figure 2:
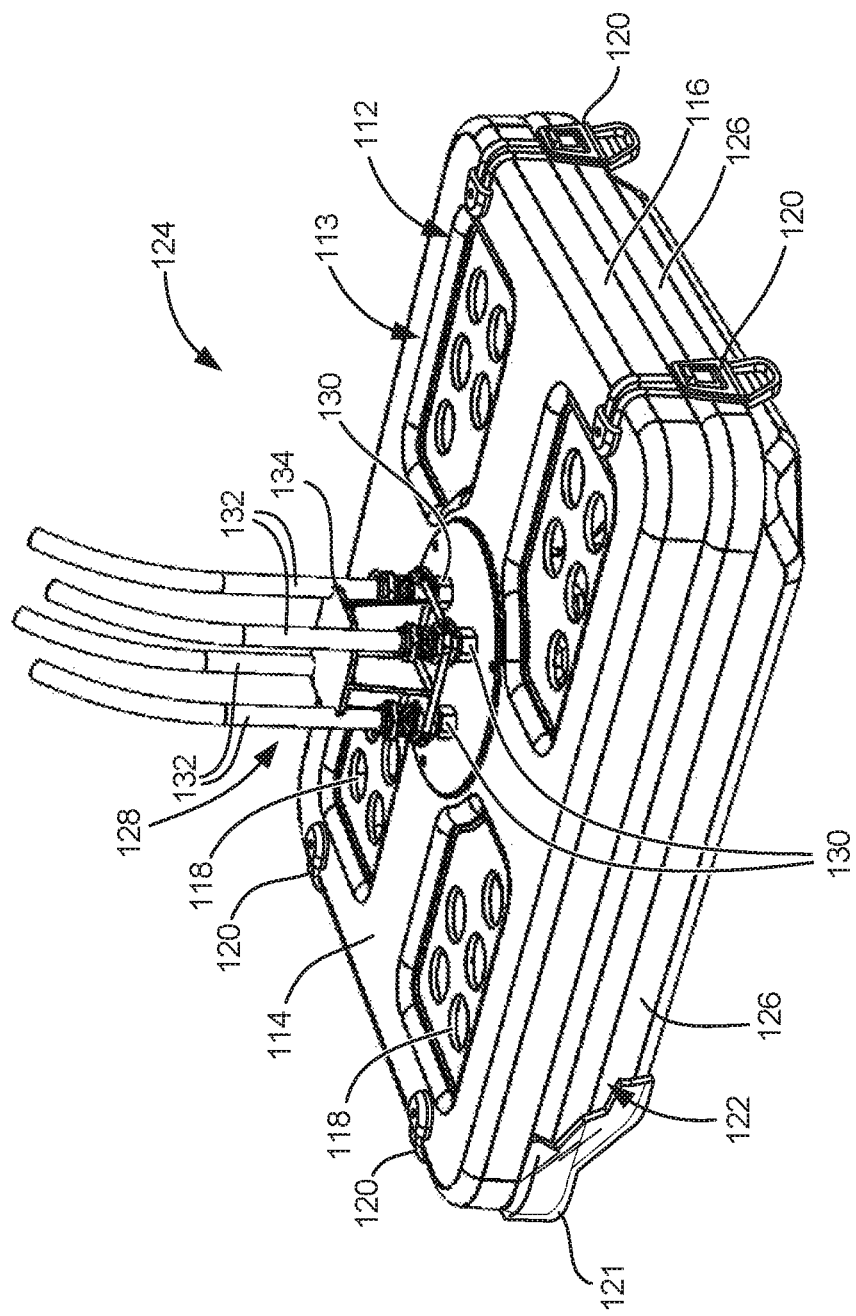
FIG. 2 is a schematic diagram of an exemplary assembled packaging assembly.

The packaging assembly 24 containing a device is positioned within decontamination chamber 12 for the decontamination of the device. FIG. 2 is a schematic diagram of the assembled packaging assembly 24, which includes a lid 112 (having an outer surface 113, central panel 114, sidewalls 116 and openings 118), fasteners 120, membrane 121, tray 122 (having a bottom 124 (not shown in FIG. 2) and sidewalls 126), lid connector assembly 128, and lid connectors 130. The sidewalls 126 of the tray 122 extend upward from the bottom 124 of the tray to define a cavity. The sidewalls 116 of the lid 112 extend downward from the central panel 114 and overlap with the sidewalls 126 of the tray 122. Membrane 121 encloses the tray 122 and is positioned between the lid 112 and the tray 122. An enclosed container interior is formed when the membrane 121 is positioned over the open top of the tray 122. In some embodiments, lid 112 can be secured to the tray 122 with one or more fasteners 120. For example, fasteners 120 may be latches, clamps or other devices which connect or hold the lid 112 to the tray 122.

The lid 112 may be formed from any suitable material. In some embodiments, the lid 112 is formed from a ridged material and two or more packaging assemblies 24 may be stack on top of one another without damaging the packaging assembly 24 or the content within the packaging. For example, the packaging assemblies 24 may be stacked before the packaging assemblies 24 are positioned within the decontamination chamber or after they are removed from the decontamination chamber. In some embodiments, the lid 112 may be formed from a material that is impermeable to the decontamination fluid. The central panel 114 of the lid 112 has an outer surface 113 which is on the outside of the packaging assembly 24 and an inner surface 115 (not shown) which is opposite the outer surface 113. When packaging 24 is assembled, outer surface 113 is exposed to the environment surrounding the packaging 24 and inner surface 115 is adjacent to the permeable membrane 121. A plurality of openings 118 are formed in the central panel 114 of the lid 112. The openings 118 are through-holes and extend from the outer surface 113 to the inner surface 115 of the lid 112. The openings 118 are located and sized to allow sufficient flow of the decontamination fluid into or out of the container interior, as described herein, during a decontamination process. In some embodiments, the openings 118 are sized and positioned such that the lid 112 has sufficient strength such that stacking two or more packaging assemblies 24 on one another does not affect the shape of packaging 24 or damage the devices positioned within.

The lid connectors 130 extend through the lid 112 and attach the lid connector assembly 128 to the central panel 114 of the lid 112. The lid connector assembly 128 includes one or more lid conduits 132 (four shown) which extend away from the lid 112. The lid connector assembly 128 may also include the conduit support assembly 134 which supports the lid conduits 132 and may improve ease of handling. In some embodiments, the conduit support assembly 134 holds the lid conduits 132 in position and improves the ease of connecting the lid conduits 132 to the lid connectors 130. The lid conduits 132 may be formed of any suitable material for use in a decontamination process. In some embodiments, the lid conduits 132 may be flexible. For example, the lid conduits 132 may be formed of a flexible polymer or plastic. In some embodiments, the lid conduits 132 may be reusable (i.e., may be used a plurality of times in decontamination processes). In other embodiments, the lid conduits 132 may be disposable and may be replaced before each decontamination process.

In some embodiments, the lid connectors 130 can include valves that may be controlled to regulate the flow of fluid through the lid conduits 132. For example, the valves may be opened or closed to allow fluid flow through or to restrict or prevent fluid flow through the lid conduits 132. The lid connectors 130 may match the size and number of lid conduits 132. Additionally or alternatively, the lid connectors 130 may match the internal diameters of the lid conduits 132. The lid connectors 130 may be fixed to the lid 112. In some embodiments, the lid connectors 130 may be removably fixed to the lid 112 and the lid connectors 130 may be removed and replaced if necessary.

The tray 122 may be formed of any suitable material. In some embodiments, the tray 122 is formed of a ridged material and multiple packaging assemblies 24 may be stacked on top of one another before and/or after the packaging assemblies 24 are positioned within the decontamination chamber or after they are removed from the decontamination chamber. In some embodiments, the tray 122 may be formed of a material that is impermeable by the decontamination fluid. For example, the tray 122 may be formed of acrylonitrile butadiene styrene (ABS). In some embodiments, tray 122 may be reusable. For example, the tray 122 may be used in a plurality of decontamination processes. In other embodiments, tray 122 may be disposed of after a first decontamination process (i.e., single-use.)

During assembly, the open top of the tray 122 is covered with the membrane 121 to form an enclosed space. In some embodiments, the membrane 121 may be in the form of a pouch which completely encloses the tray 122. For example, the tray 122 may be inserted into one end of the membrane pouch 121, which may be subsequently closed or sealed for example by an adhesive or by heat (i.e., heat seal). Alternatively, the membrane 121 may cover only a portion of the tray 122. For example, the membrane 121 may cover the top of the tray 122 and not cover the bottom 124 and/or the sidewalls 126 of the tray 122. Membrane 121 is formed of a suitable material that is permeable by the decontamination fluid and impermeable by contaminates, such that a decontaminated environment can be maintained within the container interior following a decontamination process. Suitable materials for the membrane 121 include Tyvek®, PET and Mylar®.

Figure 3:
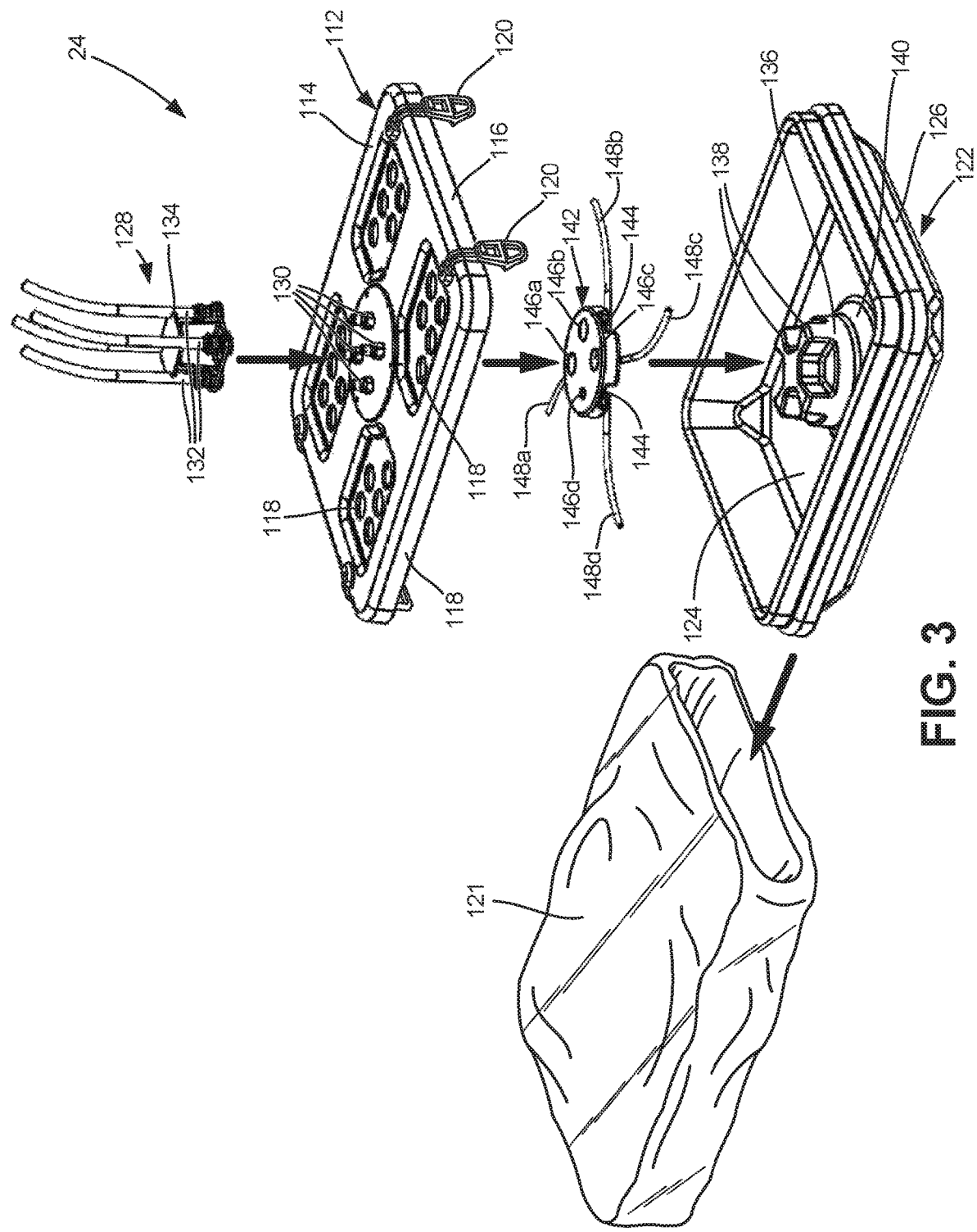
FIG. 3 is an exploded view of the packaging assembly of FIG. 2.

FIG. 3 is an exploded view of the packaging assembly 24. As shown, the interior of the tray 122 includes a hub assembly 136, which includes key projections 138 that extend upwards from a hub base 140, and a tube set assembly 142. Hub base 140 extends upward from the bottom 124 of the tray 122. In some embodiments, hub base 140 may be molded with tray 122 or may be connected to tray 122 for example with an adhesive. The hub base 140 may extend upwardly from substantially the center of the bottom 124 of the tray 122. For example, the hub base 140 may extend upwardly an equal distance from opposing sidewalls 126 in both the length and width directions.

The tube set assembly 142 connects or attaches to the hub base 140. In some embodiments, the tube set assembly 142 may be removably attached to the hub base 140. For example, the tube set assembly 142 includes key indentations 144 which correspond with key projections 138 on the hub base 140. It will be appreciated that tube set assembly 142 can connect or attach to the hub base 140 by another method.

The tube set assembly 142 includes channels 146a, 146b, 146c and 146d (collectively, channels 146) and conduits 148a, 148b, 148c and 148d (collectively, conduits 148). Conduits 148 are connected to respective channels 146 and form fluid flow paths through the tube set assembly 142. For example, one end of conduit 148a is connected to channel 146a. Similarly, conduit 148b is connected to channel 146b. The ends of conduits 148 not connected to channels 146 are configured to connect to a lumen of the lumen device. In some embodiments, channels 146 may have the same diameters and/or conduits 148 may have the same diameters. Alternatively, one or more channels 146 and/or one or more conduits 148 may have different diameters. For example, channel 146d has a smaller diameter than channel 146a and conduit 148d has a smaller inner diameter than channel 146a. In some embodiments, the diameters of the channels 146 and/or conduits 148 may be tailored or designed based on the diameters of the lumens to which they attach on the lumen device. As described herein, adjusting the diameter controls the fluid flow rate and volume through the lumen device.

In some embodiments, the conduits 148 may be flexible. For example, in some embodiments, the conduits 148 may be flexible plastic tubing. In some embodiments, the tube set assembly 142, including the hub conduits 148, is replaced each decontamination process. In other embodiments, the hub conduits 148 are replaced each decontamination process. Alternatively, the tube set assembly 142 or the hub conduits 148 may be used in multiple decontamination process.

Figure 4:
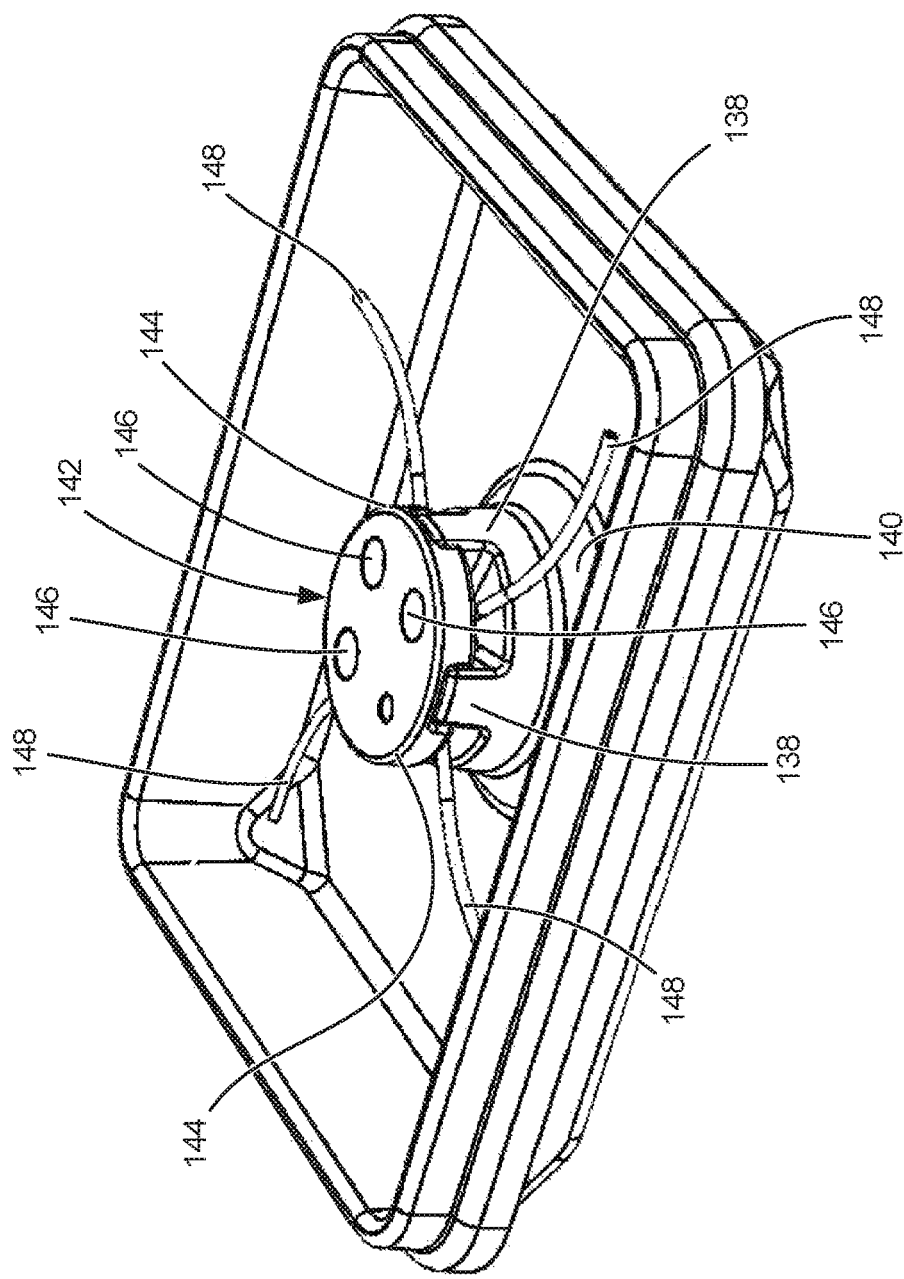
FIG. 4 is a perspective view of an exemplary tube set assembly.

FIG. 4 is a perspective view of tube set assembly 142 on or is attached to hub base 140. As shown, key projections 138 on hub base 140 fit into key indentations 144 on the tube set assembly 142. The conduits 148 connect to channels 146 and extend through at least a portion of the hub base 140. For example, conduits 148 connect to the bottom side of tube set assembly 142 and extend through openings formed between adjacent key projections 138. The free end of conduits 148 may be configured to attach to a lumen of the lumen device which is positioned within the tray 122 during a decontamination process.

Figure 5:
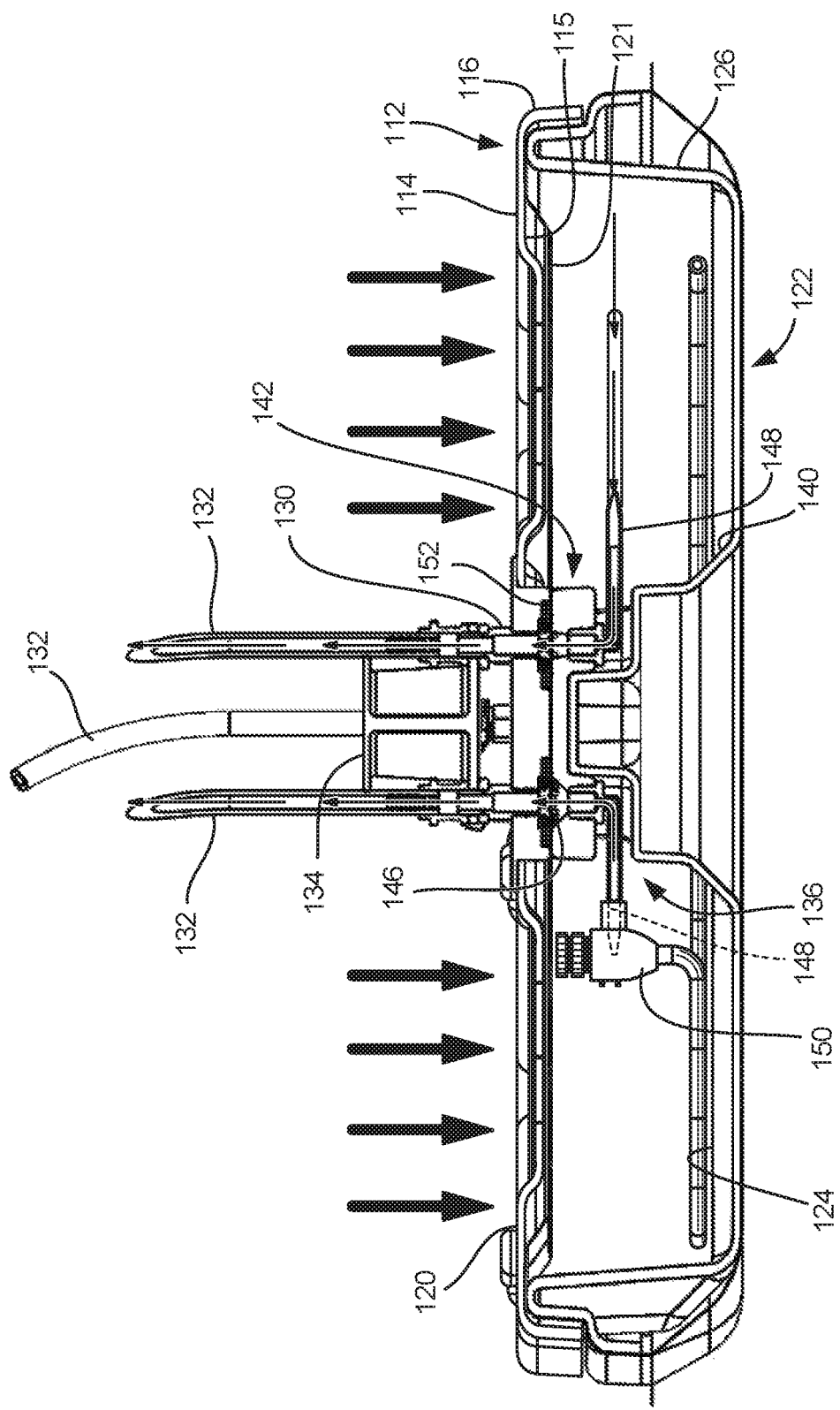
FIG. 5 is a cross-sectional view of an assembled packaging assembly.

FIG. 5 is a cross-sectional view of an assembled packaging assembly 24 for use with a lumen device 150. The lid 112 covers the top of the tray 122 to form a container interior and membrane 121 is sandwiched between the lid 112 and the tray 122. In some embodiments, the membrane 121 may cover the top of the tray 122. In other embodiments, membrane 121 may completely enclose the tray 122.

The lumen device 150 is positioned within the tray 122 and is connected to the conduit(s) 148. The lumen device 150 may contain one or more lumens, each of which may be connected to a conduit 148. Conduits 148 attach or connect to channels 146 of the tube set assembly 142. The top surface of the tube set assembly 142 interfaces with or is adjacent to the membrane 121.

On the opposite side of membrane 121 are lid connectors 130 which are in fluid communication with or are connected to the lid conduits 132. The conduits 148 of the tube set assembly 142 align with the lid conduits 132, and the membrane 121 is positioned between. An opening or other puncture is not formed in membrane 121, and a fluid flow path from the conduit 148 and the lid conduit 132 flows through membrane 121. In some embodiments, a seal 152, such as an o-ring seal, can be positioned at the interface between the lid conduit 132 and the membrane 121. Additionally or alternatively, a seal can be positioned at the interface between the tube set assembly 142 and the membrane 121.

FIG. 5 also illustrates the flow of the decontamination fluid during a decontamination cycle of a decontamination process. At the beginning of a decontamination process, the lumen device 150 is positioned within the packaging 24 and the packaging 24 is enclosed in the decontamination chamber 12. The decontamination process can include one or more decontamination cycles after which the packaging 24 is removed from the decontamination chamber 12.

During a decontamination cycle, the pressure within the decontamination chamber may be reduced. When the decontamination chamber 12 is at a desired pressure, a decontamination fluid is introduced into the decontamination chamber 12 in a suitable form, such as a vapor, fog, or gas. In some embodiments, the decontamination fluid is a provided as a gas or vapor through the vaporizer 16. The decontamination fluid within the decontamination chamber 12 will flow through openings 118 in lid 112 and permeate through the membrane 121. After permeating the membrane 121, the decontamination fluid contacts the exterior surface of the lumen device 150 within the container interior and will decontaminate the exterior surface. A portion of the decontamination fluid may also flow through at least a portion of one or more lumens of the lumen device 150. The extent or degree of decontamination depends on many factors including the concentration and chemistry of the decontamination fluid and the exposure time.

As described herein, the conduits 132 of the packaging assembly 24 are connected to the vacuum pump 14 of FIG. 1 and the conduits 148 of the tube set assembly 142 are connected to the lumens of the lumen device 150. In this way, a fluid flow path is formed from a lumen of the lumen device 150, through the hub conduit 148 and lid conduit 132 to the vacuum pump 14. After the decontamination fluid has been maintained within the decontamination chamber 12 for a period of time, the vacuum pump 14 is turned on and the decontamination fluid within the tray 122 is pulled into the lumens of the lumen device 150, through the conduits 148 and conduits 132, and out of the decontamination chamber 12.

The internal diameters of conduits 132 and 148 may be sized to control the fluid flow rate of the decontamination fluid through the lumens of lumen device 150. In some embodiments, the size of the conduit 132 and conduit 148 are sized in relation to the size of the lumen of the lumen device 150 to which it is attached. For example, a smaller internal diameter conduit 148 may be attached to a smaller diameter lumen of device 150 and a larger internal diameter conduit 148 may be attached to a larger diameter lumen.

The decontamination cycle may be repeated. That is, decontamination fluid may be introduced into and removed from the decontamination chamber 12 two or more times. The decontamination process, which includes one or more decontamination cycles, achieves a desired level of decontamination of the lumen device 150. As described herein, the packaging 24 may be substantially strong enough to enable multiple packaging assemblies 24 to be stacked on one another before or after the decontamination process. Additionally, the membrane 121 encloses at least the top of the tray 122 and maintains a decontaminated environment within the tray cavity following the decontamination process. In some embodiments, the lid 112 may be removed after the decontamination process. Alternatively, the packaging 24 may be stored following the decontamination process with the lid 112 attached to the tray 122.

Figure 6:
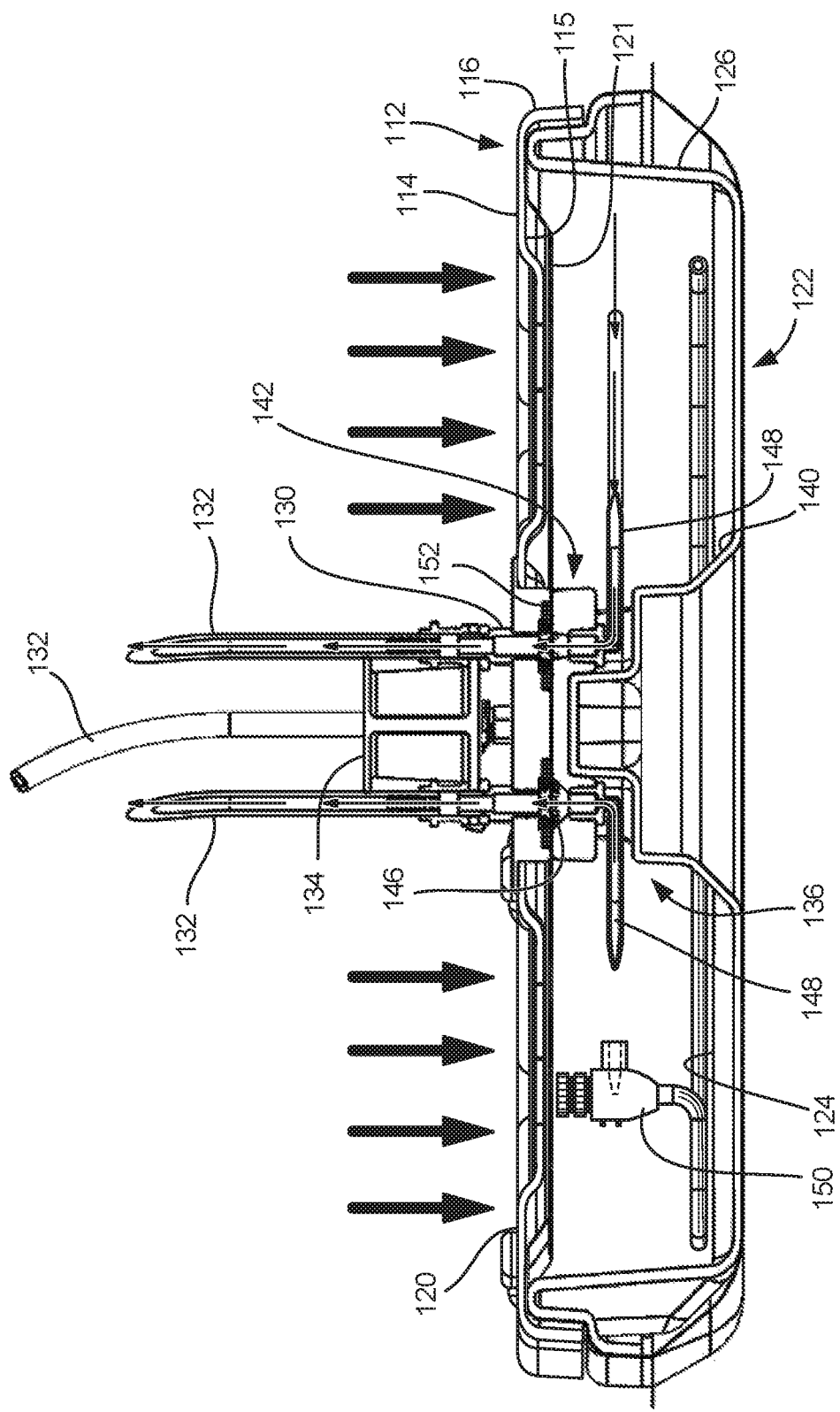
FIG. 6 is a cross-sectional view of an assembled packaging assembly.

FIG. 6 is a cross-sectional view of an assembled packaging assembly 24 in which the lumen device 150 is positioned within the tray 122 and is adjacent to and spaced apart from the conduit(s) 148 of the tube set assembly 142. The lumens of the lumen device 150 are not physically connected to a conduit 148. Rather, the conduits 148 are in direct communication with the environment within the tray 122. In this way a fluid flow path is formed from the interior of the tray 122 through the hub conduit(s) 148 and lid conduit(s) 132 to the vacuum pump 14. During a decontamination process, decontamination fluid is introduced into the decontamination chamber 12. When the vacuum pump is turned on, decontamination fluid within the tray 122 is pulled through the conduits 148 and conduits 132 and, finally, out of the decontamination chamber 12. As the decontamination fluid is evacuated from the tray 122 by the vacuum pump 14, decontamination fluid within the decontamination chamber 12 but outside of the tray 122 is drawn into the tray 122. A portion of the decontamination fluid may also be pulled through the lumens as the fluid flows through the tray. In this way, the assembled packaging assembly 24 results in an increased flow of decontamination fluid through the packaging as compared to a system without conduits 148 and 132. Assembled packaging assembly 24 may also result in increased contact between the lumen device 150 and the decontamination fluid.

Figure 7:
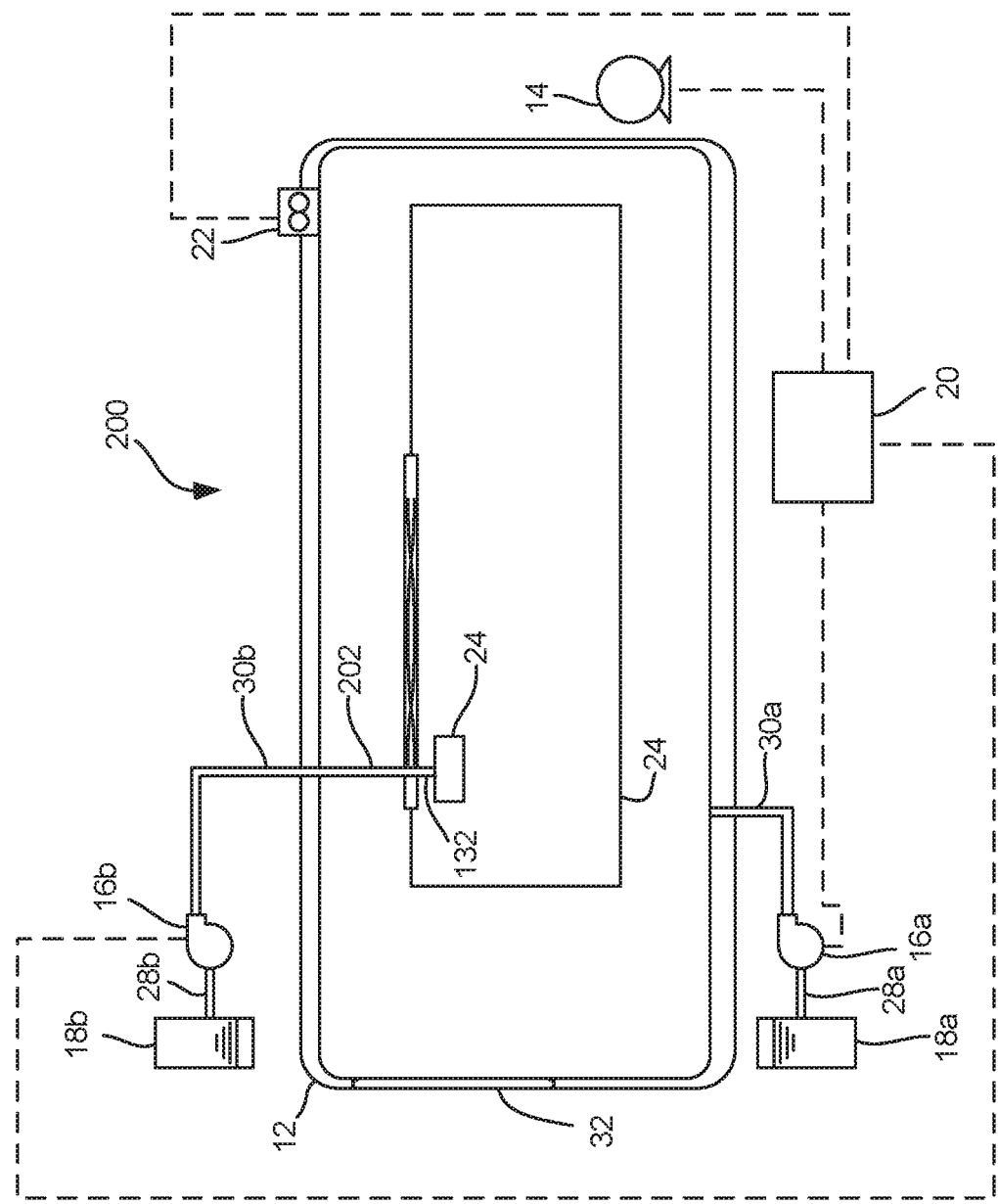
FIG. 7 is a schematic diagram of another exemplary decontamination system.

In alternative embodiments, such as system 200 which is schematically illustrated in FIG. 7, the conduits 132 are connected to a vaporizer 16b. In some embodiments, the conduits 148 of the tube set assembly 142 are connected to the lumens of the lumen device 150. In this way, a fluid flow path is formed from the vaporizer 16b through conduit 200 and the lid conduit 132 to the lumen device 150. In a decontamination process, decontamination fluid is introduced into the decontamination chamber 12 by vaporizer 16a, vaporizer 16b or by both vaporizers. When the vaporizer 16b is activated, the decontamination fluid flows through conduit 202 and the lid conduit 132 to the packaging assembly 24. As described herein, the decontamination fluid flows through the lid conduit 132, the membrane 121, and into the packaging assembly 24 containing a lumen device 150. In some embodiments, one or more lumens of the lumen device 15 is/are physically connected to conduit 148. In other embodiments, the lumens of the lumen device 15 are spaced apart from and are not physically connected to a conduit 148.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The following is claimed:

1. An apparatus for use in a method of decontaminating a device with a decontaminating fluid, the apparatus comprising:
   a tray having a bottom and sidewalls extending upwardly from the bottom to define a cavity;
   a membrane permeable by the decontaminating fluid positioned over the top of the tray to form an enclosed space;
   a lid secured to the tray by fasteners with the membrane positioned between the tray and the lid, the lid having a central panel and sidewalls extending downward from the central panel;
   a hub assembly positioned within the cavity, the hub assembly including a hub extending upwardly from the bottom of the tray and a hub conduit having a first end and a second end adjacent to the membrane; and
   a lid connector assembly including a lid conduit, the lid conduit having a first end adjacent to the membrane and aligned with the second end of the hub conduit.

2. The apparatus of claim 1, wherein the lid connector assembly and the hub assembly each contain two or more conduits and each lid conduit aligns with a corresponding hub conduit.

3. The apparatus of claim 2, wherein at least one of the lid conduits has a different diameter than another lid conduit.

4. The apparatus of claim 1, wherein the hub extends upwardly from substantially a center of the bottom.

5. The apparatus of claim 1, wherein the membrane completely encloses the tray.

6. The apparatus of claim 1 and further comprising: a seal positioned between the first end of the lid conduit and the membrane.

7. The apparatus of claim 1, wherein the lid is formed of a first material that is impermeable by the decontaminating fluid and the tray is formed of a second material that is impermeable by the decontaminating fluid.

8. The apparatus of claim 1, wherein the first end of the hub conduit is attachable to a lumen of the device positioned within the cavity.

9. The apparatus of claim 1, wherein a fluid flow path is formed through the hub conduit and the lid conduit and wherein the membrane is within the fluid flow path.

10. The apparatus of claim 1, wherein the hub assembly further comprises a tube set assembly removably connected to the hub conduit and removably connected to the hub.

11. A method of decontaminating a device with a decontamination fluid, the method comprising:
    placing the device in a tray having a hub conduit connected to a hub extending upwardly from a bottom of the tray;
    covering at least a top of the tray with a membrane permeable by the decontaminating fluid to form an enclosed space;
    securing a lid to the tray with the membrane positioned between the tray and the lid and a first end of a lid conduit of a lid port assembly adjacent to the membrane and aligned with a second end of the hub conduit; and
    positioning the tray with the lid secured into a decontamination chamber.

12. The method of claim 11, and further comprising:
    introducing the decontamination fluid into the decontamination chamber; and
    evacuating the decontamination fluid from the decontamination chamber through a flow path formed by a lumen device, the hub conduit and the lid conduit.

13. The method of claim 12, wherein the lid includes a central panel having a plurality of openings and the decontamination fluid permeates through the membrane and into the enclosed space.

14. The method of claim 12, and further comprising:
    removing the tray from the decontamination chamber after a decontamination process; and
    storing the tray with the lid removed after the decontamination process.

15. The method of claim 11, wherein the lid port assembly and the hub assembly each contain two or more conduits and each lid conduit aligns with a corresponding hub conduit when the lid is secured to the tray.

16. The method of claim 15, and further comprising:
    connecting a first end of each hub conduit to a lumen of the device.

17. The method of claim 11, wherein a second end of the lid conduit is connected to a vacuum pump.

18. The method of claim 11, wherein the covering at least the top of the tray with a membrane includes completely enclosing the tray within the membrane.

19. The method of claim 11, wherein a seal is positioned between the first end of the lid conduit and the membrane.

20. The method of claim 11, and further comprising:
    removing the hub conduit from the hub after removing the device from the tray.

* * * * *